United States Patent
Rohde et al.

(10) Patent No.: US 10,265,454 B2
(45) Date of Patent: Apr. 23, 2019

(54) DIALYSIS SYSTEM WITH FLOW REGULATION DEVICE

(75) Inventors: Justin B. Rohde, Des Plaines, IL (US); Shincy J. Maliekkal, Glenview, IL (US)

(73) Assignees: Baxter International Inc., Deerfield, IL (US); Baxter Healthcare SA, Glattpark (Opfikon) (CH)

(*) Notice: Subject to any disclaimer, the term of this patent is extended or adjusted under 35 U.S.C. 154(b) by 558 days.

(21) Appl. No.: 12/180,324

(22) Filed: Jul. 25, 2008

(65) Prior Publication Data

US 2010/0018923 A1    Jan. 28, 2010

(51) Int. Cl.
*B01D 61/32* (2006.01)
*A61M 1/16* (2006.01)

(52) U.S. Cl.
CPC ........ *A61M 1/1656* (2013.01); *A61M 1/1635* (2014.02)

(58) Field of Classification Search
CPC .......................... A61M 1/1635; A61M 1/1656
See application file for complete search history.

(56) References Cited

U.S. PATENT DOCUMENTS

| | | |
|---|---|---|
| 422,936 A | 3/1890 | Hanson |
| 1,627,257 A | 5/1927 | Stevens |
| 2,307,566 A | 1/1943 | Browne |
| 2,315,179 A | 3/1943 | Allender |
| 2,393,838 A | 1/1946 | Tarbox |
| 2,474,512 A | 6/1949 | Bechtold et al. |
| 2,565,374 A | 8/1951 | Kitchel |
| 2,773,455 A | 12/1956 | Mercier |
| 2,927,658 A | 3/1960 | Slater, Jr. |
| 3,252,623 A | 5/1966 | Corbin et al. |
| 3,527,700 A | 9/1970 | Goldhaber |
| 3,658,445 A | 4/1972 | Pulman et al. |
| 3,741,692 A | 6/1973 | Rupp |

(Continued)

FOREIGN PATENT DOCUMENTS

| | | |
|---|---|---|
| EP | 0 816 677 | 1/1998 |
| GB | 2181494 | 4/1987 |

(Continued)

OTHER PUBLICATIONS

International Search Report and Written Opinion for International Application No. PCT/US2009/047585 dated Feb. 1, 2010.

(Continued)

*Primary Examiner* — Dirk R Bass
(74) *Attorney, Agent, or Firm* — K&L Gates LLP

(57) ABSTRACT

A dialysis system includes a dialysis machine with a variable fluid demand including at least a lower demand and a higher demand. A fluid source is in fluid communication with the dialysis machine and provides fluid to the dialysis machine at a fluid flow rate. A flow regulation device includes a fluid inlet in fluid communication with the fluid source and a fluid outlet in fluid communication with the dialysis machine. The flow regulation device is operable to expand and contract to provide a variable internal volume. The flow regulation device expands when the dialysis machine has the lower demand and contracts when the dialysis machine has the higher demand.

28 Claims, 4 Drawing Sheets

(56) References Cited

U.S. PATENT DOCUMENTS

| | | |
|---|---|---|
| 3,778,195 A | 12/1973 | Bamberg |
| 3,804,107 A | 4/1974 | Kozlov et al. |
| 3,805,817 A * | 4/1974 | Smith .............................. 137/8 |
| 3,818,934 A | 6/1974 | Borsanyi |
| 3,902,490 A | 9/1975 | Jacobsen et al. |
| 3,974,854 A | 8/1976 | Kurpanek |
| 3,986,956 A | 10/1976 | Anno |
| 4,003,379 A | 1/1977 | Ellinwood, Jr. |
| 4,077,405 A | 3/1978 | Hoerten et al. |
| 4,081,372 A | 3/1978 | Atkin et al. |
| 4,107,039 A | 8/1978 | Lindsay, Jr. et al. |
| 4,191,184 A | 3/1980 | Carlisle |
| 4,193,068 A | 3/1980 | Ziccardi |
| 4,209,014 A | 6/1980 | Sefton |
| 4,258,711 A | 3/1981 | Tucker et al. |
| 4,293,961 A | 10/1981 | Runge |
| 4,345,594 A | 8/1982 | Bisera et al. |
| 4,360,019 A | 11/1982 | Portner et al. |
| 4,360,324 A | 11/1982 | Ohara et al. |
| 4,392,791 A | 7/1983 | Mandroian |
| 4,445,829 A | 5/1984 | Miller |
| 4,489,750 A | 12/1984 | Nehring |
| 4,493,706 A | 1/1985 | Bolsanyi et al. |
| 4,525,165 A | 6/1985 | Fischell |
| 4,599,165 A | 7/1986 | Chevallet |
| 4,604,090 A | 8/1986 | Reinicke |
| 4,610,702 A * | 9/1986 | Krantz .............................. 96/99 |
| 4,653,987 A | 3/1987 | Tsuji et al. |
| 4,662,829 A | 5/1987 | Nehring |
| 4,671,792 A | 6/1987 | Borsanyi |
| 4,673,391 A | 6/1987 | Kondo et al. |
| 4,684,368 A | 8/1987 | Kenyon |
| 4,687,423 A | 8/1987 | Maget et al. |
| 4,687,468 A | 8/1987 | Gianturco |
| 4,714,462 A | 12/1987 | DiDomenico |
| 4,728,265 A | 3/1988 | Cannon |
| 4,741,678 A | 5/1988 | Nehring |
| 4,744,786 A | 5/1988 | Hooven |
| 4,767,526 A | 8/1988 | Vantard |
| 4,838,887 A | 6/1989 | Idriss |
| 4,871,351 A | 10/1989 | Feingold |
| 4,954,046 A | 9/1990 | Irvin et al. |
| 4,969,936 A * | 11/1990 | Schweigert et al. ............ 96/129 |
| 4,978,338 A | 12/1990 | Melsky et al. |
| 4,979,441 A | 12/1990 | Welch et al. |
| 5,053,031 A | 10/1991 | Borsanyi |
| 5,057,081 A | 10/1991 | Sunderland et al. |
| 5,088,904 A | 2/1992 | Okada |
| 5,152,680 A | 10/1992 | Okada |
| 5,176,644 A | 1/1993 | Srisathapat et al. |
| 5,244,463 A | 9/1993 | Cordner, Jr. et al. |
| 5,247,434 A | 9/1993 | Peterson et al. |
| 5,263,935 A | 11/1993 | Hessel |
| 5,290,158 A | 3/1994 | Okada |
| 5,387,188 A * | 2/1995 | Watson .............................. 604/8 |
| 5,421,208 A | 6/1995 | Packard et al. |
| 5,544,651 A | 8/1996 | Wilk |
| 5,552,998 A | 9/1996 | Datta |
| 5,554,011 A | 9/1996 | Bales et al. |
| 5,562,429 A | 10/1996 | Romstad et al. |
| 5,591,344 A * | 1/1997 | Kenley et al. ................ 210/636 |
| 5,607,418 A | 3/1997 | Arzbaecher |
| 5,730,722 A | 3/1998 | Wilk |
| 5,817,076 A | 10/1998 | Fard |
| 5,868,168 A | 2/1999 | Mott et al. |
| 5,871,478 A | 2/1999 | Berrigan |
| 6,058,958 A | 5/2000 | Benkowski et al. |
| 6,089,837 A | 7/2000 | Cornell |
| 6,110,427 A * | 8/2000 | Uffenheimer .................. 422/81 |
| 6,159,160 A | 12/2000 | Hsei et al. |
| 6,234,773 B1 | 5/2001 | Hill et al. |
| 6,280,408 B1 | 8/2001 | Sipin |
| 6,290,681 B1 | 9/2001 | Brown |
| 6,305,919 B1 | 10/2001 | Staton et al. |
| 6,312,409 B1 | 11/2001 | Gross |
| 6,319,245 B1 | 11/2001 | Berrigan |
| 6,386,046 B1 | 5/2002 | Mattar |
| 6,471,686 B1 | 10/2002 | Berrigan |
| 6,537,268 B1 | 3/2003 | Gibson et al. |
| 6,558,343 B1 | 5/2003 | Neftel |
| 6,638,263 B1 | 10/2003 | Theeuwes et al. |
| 6,669,455 B2 | 12/2003 | Welch |
| 6,723,062 B1 | 4/2004 | Westberg et al. |
| 6,746,606 B2 | 6/2004 | Pfeil et al. |
| 6,837,693 B2 | 1/2005 | Welch |
| 6,861,033 B2 | 3/2005 | Mullins et al. |
| 6,997,942 B2 | 2/2006 | Machold et al. |
| 7,018,361 B2 | 3/2006 | Gillespie, Jr. et al. |
| 7,018,375 B2 | 3/2006 | Berrigan |
| 7,025,750 B2 | 4/2006 | Brugger et al. |
| 7,048,522 B2 | 5/2006 | Bradford, Jr. |
| 7,150,711 B2 | 12/2006 | Nusser et al. |
| 7,175,649 B2 | 2/2007 | Machold et al. |
| 7,208,092 B2 | 4/2007 | Micheli |
| 7,241,378 B2 | 7/2007 | Ikeda |
| 7,326,564 B2 | 2/2008 | Lundell et al. |
| 2002/0088752 A1 | 7/2002 | Balschat et al. |
| 2002/0127736 A1 | 9/2002 | Chou et al. |
| 2003/0195454 A1 | 10/2003 | Wariar |
| 2004/0019320 A1 | 1/2004 | Childers et al. |
| 2004/0082903 A1 | 4/2004 | Micheli |
| 2005/0038325 A1 | 2/2005 | Moll |
| 2006/0236756 A1 * | 10/2006 | Rinaldi et al. ............... 73/53.01 |
| 2007/0135758 A1 | 6/2007 | Childers et al. |
| 2007/0158267 A1 | 7/2007 | Micheli |
| 2007/0278155 A1 * | 12/2007 | Lo et al. ....................... 210/646 |
| 2008/0015493 A1 | 1/2008 | Childers et al. |

FOREIGN PATENT DOCUMENTS

| | | |
|---|---|---|
| WO | 2005/025726 | 3/2005 |
| WO | 2006/008866 | 1/2006 |

OTHER PUBLICATIONS

International Search Report and Written Opinion for International Application No. PCT/US2009/030299 dated May 29, 2009.

International Search Report and Written Opinion for PCT/US2008/066101 dated Feb. 12, 2009.

Non-Final Office Action for U.S. Appl. No. 11/941,840 dated Jul. 24, 2009.

Final Office Action for U.S. Appl. No. 11/941,840 dated Feb. 8, 2010.

Non-Final Office Action for U.S. Appl. No. 11/941,840 dated Sep. 17, 2010.

Notification of Transmittal of the International Preliminary Report on Patentability for International Application No. PCT/US2009/047585 dated Oct. 12, 2010.

Mexican Office Action received by foreign associate dated Aug. 8, 2013 for related Mexican Appln. No. MX/a/2011/000977.

Canadian Office Action dated Jul. 17, 2015 in corresponding Canadian Patent Application No. 2,730,263 (4 pages).

European Office Action—Appl. No. 09-789833-2-1651 dated Dec. 5, 2016—3 pages.

* cited by examiner

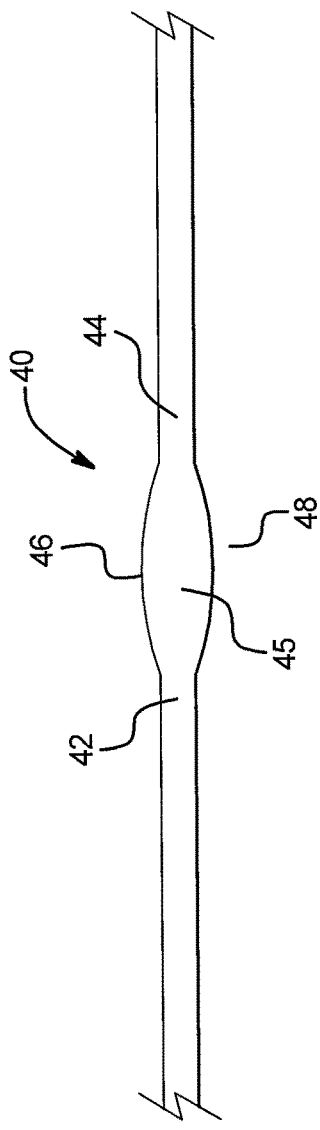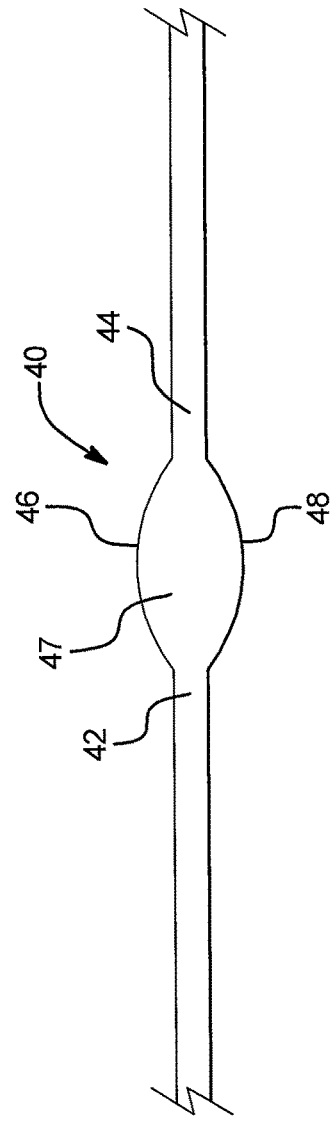

DIALYSIS SYSTEM WITH FLOW REGULATION DEVICE

BACKGROUND

The present disclosure relates generally to a dialysis system. More specifically, the present disclosure relates to a dialysis system including a flow regulation device for regulating the fluid flow to a dialysis device.

Hemodialysis uses a dialysis fluid to remove waste products from a patient's blood. One of the drawbacks of performing home hemodialysis (hemodialysis in a patient's home) is the need for a dedicated water treatment, which includes equipment, water connection and drainage. Installing and using those components is a difficult and cumbersome task that can require a patient's home to be modified. Nevertheless, there are benefits to daily hemodialysis treatments versus bi- or tri-weekly visits to a treatment center. In particular, a patient receiving more frequent treatments removes more toxins, waste products, and excess water more frequently, thus reducing fluctuations in blood chemistry and blood pressure, than a patient receiving less frequent but perhaps longer treatments.

Peritoneal dialysis utilizes a sterile dialysis solution, which is infused into a patient's peritoneal cavity and into contact with the patient's peritoneal membrane. Waste, toxins and excess water pass from the patient's bloodstream through the peritoneal membrane and into the used dialysate. The spent dialysate is later drained from the patient's peritoneal cavity to remove the waste, toxins and excess water from the patient. Patients undergoing peritoneal dialysis also face difficulties in terms of the volume of treatment fluid needed.

Dialysis machines require large (ranging from 20 to 200 liters per treatment) amounts of water to provide the dialysis fluid used in the machine. Further, the fluid demand of a dialysis machine is not constant and varies with the cycling of the machine. In the institutional setting, most water systems for dialysis supply a hydraulic branch with very large volumes of water. The excess water and large number of individual dialysis systems connected to the branch mitigate the variable fluid demand of each individual machine. Moreover, many water systems include large tanks capable of holding several thousand liters to provide a backup reservoir to account for changes in draw rate.

In a home setting, a single dialysis device may be connected to a single water supply without any fluid reservoir in the circuit. Thus, the device lacks the water reserve capabilities previously described for systems with large numbers of dialysis machines. Because dialysis machines do not draw a constant flow of water but rather start and stop, problems are presented. The fluid supply to the device needs to have a flow capacity that is at least as great as the maximum instantaneous draw rate of the dialysis device, which can be significantly greater than the average fluid demand of the dialysis device. Further, if the water source provides a continuous flow of fluid, a significant amount of dialysis fluid is produced but not used for dialysis, and thus is wasted.

SUMMARY

The present disclosure provides a dialysis system including a flow regulation device for regulating the fluid flow to the dialysis device.

In an embodiment, a dialysis system includes a dialysis machine with a variable fluid demand including at least a lower demand and a higher demand. A fluid source is in fluid communication with the dialysis machine and provides fluid to the dialysis machine at a fluid flow rate. A flow regulation device includes a fluid inlet in fluid communication with the fluid source and a fluid outlet in fluid communication with the dialysis machine. The flow regulation device is operable to expand and contract to provide a variable internal volume. The flow regulation device expands when the dialysis machine has the lower demand and contracts when the dialysis machine has the higher demand. The fluid may be dialysate or purified water.

In an embodiment, the flow regulation device includes a first wall and a second wall disposed opposite each other between the fluid inlet and the fluid outlet to define in part the internal volume, wherein the first wall and the second wall are composed of a compliant material. The first wall and the second wall move away from each other when the device expands and move towards each other when the device contracts.

In another embodiment, the flow regulation device includes a pleated wall, the pleated wall expanding outwardly to provide the variable internal volume.

In an embodiment, the maximum internal volume of the flow regulation device is between 25 mL and 200 mL. The maximum internal volume of the flow regulation device may be between 50 ml and 100 ml.

In an embodiment, the fluid source comprises a system for preparing the fluid from a water source.

In an embodiment, the fluid flow rate from the fluid source is generally constant. The fluid flow rate from the fluid source may be generally equal to an average fluid demand of the dialysis machine.

In an embodiment, the dialysis machine is a hemodialysis machine.

In another embodiment, a dialysis system includes a flow regulation device that contains a gas providing a gas volume. The gas volume is regulated to provide a variable fluid volume. The flow regulation device provides a maximum fluid volume between 25 mL and 200 mL. The gas volume decreases when the dialysis machine has the lower demand and increases when the dialysis machine has the higher demand.

In an embodiment, the flow regulation device comprises a rigid canister. The gas volume may be regulated by discharging gas from the flow regulation device and taking gas into the flow regulation device. The dialysis system may include a filter for filtering gas entering the flow regulation device.

In another embodiment, a dialysis system includes a dialysis machine with a variable fluid demand. A fluid source is in fluid communication with the dialysis machine and provides fluid to the dialysis machine at a fluid flow rate. A controller is in communication with the dialysis machine and configured to send a control signal indicative of a fluid demand of the dialysis machine. A flow control mechanism is in communication with the controller and operable to receive the control signal to control the fluid flow rate based on the fluid demand of the dialysis machine.

In another embodiment, a method of controlling the flow of fluid to a dialysis machine includes providing the dialysis machine. The dialysis machine has a variable fluid demand including at least a lower demand and a higher demand. A fluid source is in fluid communication with the dialysis machine and provides fluid to the dialysis machine. A flow control mechanism is provided to control flow from the fluid source. The flow of fluid to the dialysis machine is controlled by sending a signal from the dialysis machine, wherein the signal is indicative of a fluid demand of the dialysis machine, and using the signal to regulate the flow control mechanism to control the fluid flow based on the fluid demand of the dialysis machine.

In an embodiment, the signal is indicative of a current fluid demand of the dialysis machine. Alternatively, the signal is indicative of an anticipated future fluid demand of the dialysis machine.

In an embodiment, the dialysis machine includes a pump and a pump controller, wherein the signal is provided by the pump controller. The signal may be provided by wire. Alternatively, the signal may be provided wirelessly.

Additional features and advantages are described herein, and will be apparent from the following Detailed Description and the figures.

BRIEF DESCRIPTION OF THE FIGURES

FIG. 3 illustrates an embodiment of a flow regulation device in a first configuration.

FIG. 4 illustrates the flow regulation device of FIG. 2 in a second configuration.

DETAILED DESCRIPTION

The present disclosure is directed to a flow regulation device for making dialysis easier for a dialysis patient at home. While the embodiments discussed are not limited to home applications, it will be readily apparent that an efficient, safe, and conveniently-sized dialysis system is most useful in a home application. Nevertheless, the systems disclosed herein may also be used in larger institutions, such as hospitals or clinics, and may be used as back-up or reserve capacity in the event that the supply chain is somehow interrupted.

Figure 1:
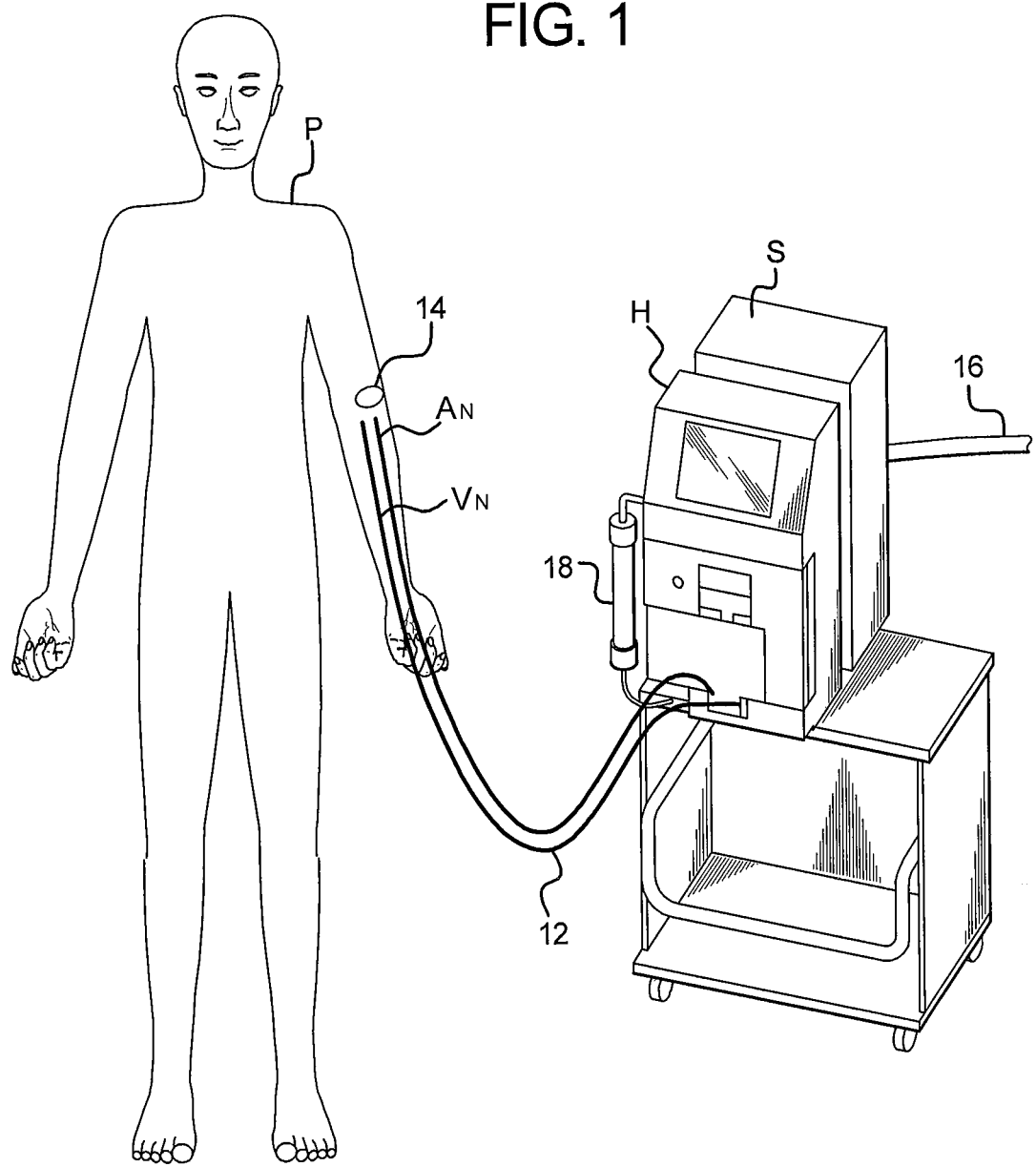
FIG. 1 depicts a perspective view of a dialysis system.

A general hemodialysis system is depicted in FIG. 1. Patient P is undergoing hemodialysis with hemodialysis machine 20, which may be a home hemodialysis machine. The patient is connected to the hemodialysis machine via tubing 12, arterial and venous access needles $A_N$ and $V_N$, and access site 14. The hemodialysis machine H pumps fresh dialysate from a fluid source, which may be provided by the system for preparing dialysis solution described below. Tubing 16 conveys fresh dialysate from a dialysis source to a dialysate pump in the hemodialysis machine, and then to the dialyzer 18. A system for administering peritoneal dialysis using fresh dialysate fluid may be used instead.

Figure 2:
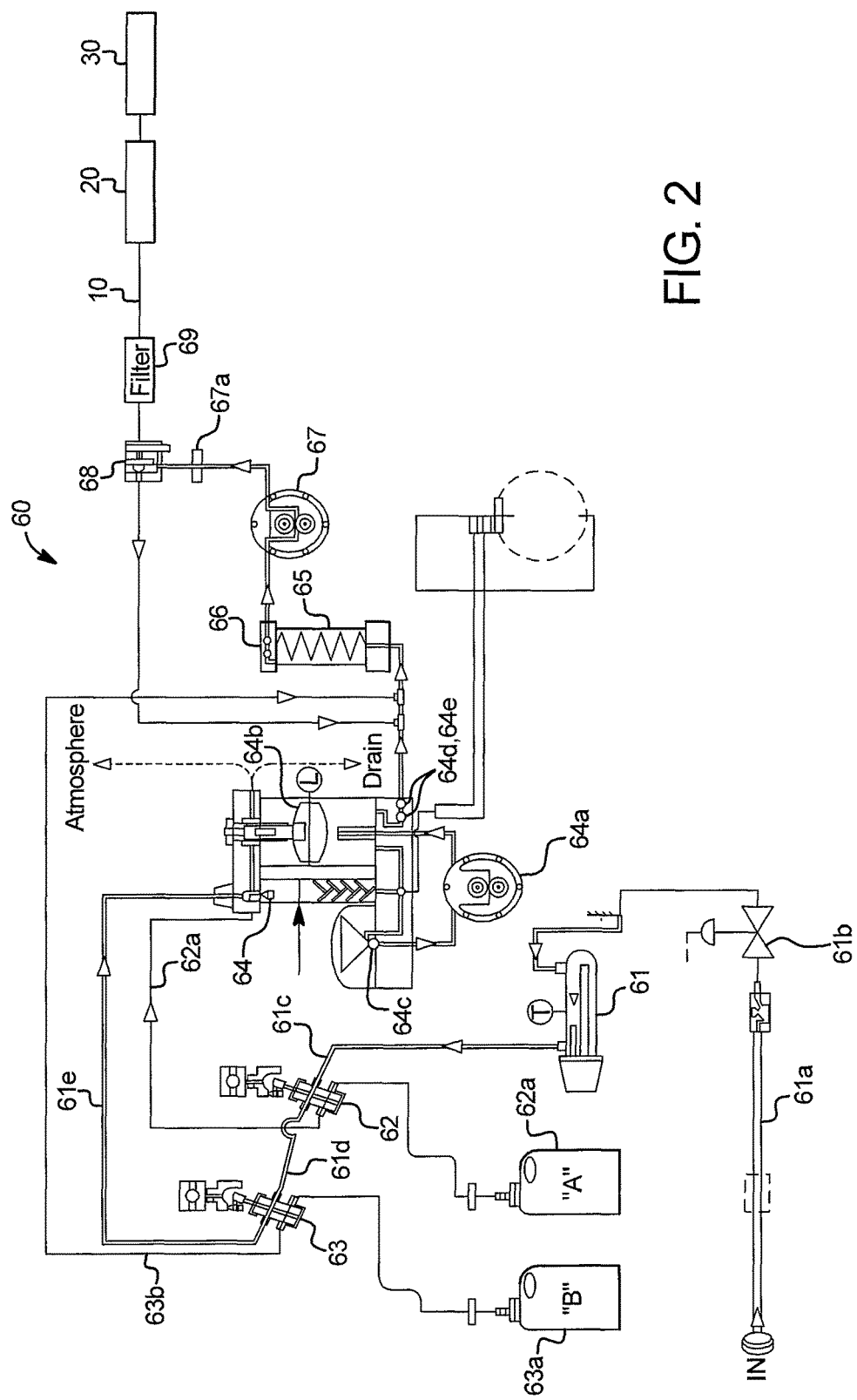
FIG. 2 is an embodiment of a dialysis system including a system for preparing dialysis solution.

As shown in FIG. 2, the dialysis system includes a fluid source 10, a flow regulation device 20, and a dialysis machine 30. The fluid source may be the system 60 (described below) for producing dialysis fluid, or another suitable fluid source. Alternatively, the dialysis fluid can be produced in the dialysis machine 30, and the fluid source may supply the dialysis machine 30 with purified water for dialysis. The dialysis machine 30 has a variable fluid demand. The fluid source 10 is in fluid communication with the dialysis machine 20 and provides dialysis fluid to the dialysis machine 30. When the dialysis system is in the no flow or lower flow parts of a pump cycle, the flow regulation device 20 is filled with dialysis fluid or purified water from the fluid source 10. When the dialysis device 30 initiates the high flow portion of the pump cycle, the volume of fluid in the flow regulation device 20 is decreased. Thus, the flow regulation device 20 acts as a damper to reduce the pulsatility, or variations in fluid demand, that the fluid supply 10 is exposed to.

One system 60 for producing dialysate to provide fluid for the dialysis fluid source 10 is depicted in FIG. 2. System 60 receives purified water for dialysis through line 61a and control valve 61b. The water is heated, if desired, using in-line heater 61. The heated water flows through lines 61c, 6 ld to A and B concentrate pumps 62, 63, for pumping concentrate respectively from reservoirs 62a, 63a. The pumps are positive displacement pumps, such as gear pumps, vane pumps, or piston pumps, to pump precise amounts of A or B concentrate. One embodiment uses small ceramic piston pumps, available from Fluid Metering, Inc., Long Island, N.Y., U.S.A. U.S.A. Other pumps may be used. Other embodiments use proportioning or ratiometric pumps, whose flow of A or B concentrate may be set, and which thereafter pump A and B concentrate in a ratio proportional to the distilled water metered out. A controller for the system keeps track of the amounts of concentrate pumped, and also keeps track of the amount of deaerated water and A that is pumped, thus keeping precisely proportioned flows.

In this embodiment, the A concentrate pump 62 pumps A concentrate to mixing vessel 64 through line 62a, the vessel not filled but retaining an air gap at its top, while the correct ratio of water also flows to the vessel through line 61e. After the water and the A concentrate are mixed, the mixture is deaerated by spraying using precision metering pump 64a, nozzle 64c, and air trap 64b. Other embodiments such as a simple restriction creating a starved intake to pump 64a, could be substituted for the sprayer to remove the air from the solution. The mixture is monitored by temperature and conductivity sensors 64d, 64e. Vessel 64 includes a level sensor L. The deaerated acid mixture is then sent to the B mix chamber 65, where B concentrate from the B concentrate pump through line 63b is added, in this case in-line. The B mix chamber 65 is equipped with a second conductivity sensor 66 to monitor the quality of the finished dialysis solution.

The dialysis solution is then pumped by supply pump 67 through filter 67a, to remove particles larger than 150μ. Control valve 68 controls the flow of dialysis solution from system 60. If the correct level of continuity has not been achieved, the freshly-prepared dialysis solution may be recycled as desired through the filter and the mixing chamber, as shown, until the proper mixing and purity has been achieved. The dialysis solution can then be pumped through a final filter, endotoxin filter 69, on its way to being used. The endotoxin filter is intended to remove endotoxins and bacteria, or fragments of bacteria, such as *E. coli* and *P. aeruginosa*. This filter could be an ultrafilter such as those made by Medica Mirandolla Italy or a charged membrane microfilter such as those made by Pall, Long Island, N.Y., USA.

The process described above is only one method for preparing a dialysis solution. Other dialysis solutions may be used, including those requiring an osmotic agent, such as a small amount of dextrose, glucose, sodium or potassium polyacrylate, or mixtures of these, or other component. These solutions are prepared in generally similar ways, some embodiments using powders, some using concentrates, some using solutions. Any such embodiments are intended to fall within the scope of the present disclosure. Embodiments using powders may require a conventional stirred-tank vessel, or vessel suitable for mixing powders using a stirrer or using flow, often turbulent flow, to insure a good mixing. For home use, this may be any suitable mixer capable of maintaining and preserving sterility.

FIG. 3 shows an embodiment 40 of the flow regulation device. The flow regulation device 40 is disposed between the fluid source 10 and the dialysis machine 30. Flow regulation device 40 includes a fluid inlet 42 in fluid communication with the fluid source 10 and a fluid outlet 44 in fluid communication with the dialysis machine 30. The flow regulation device 40 is operable to expand and contract to provide a variable internal volume. The flow regulation device 40 expands when the dialysis machine 30 has a lower demand and contracts when the dialysis machine 30 has a higher demand. FIG. 4 shows the flow regulation device 40 in a second configuration with a larger internal volume 47 than the internal volume 45 of the flow regulation device 40 in the first configuration shown in FIG. 3.

The flow regulation device 40 includes a first wall 46 and a second wall 48 disposed opposite each other between the fluid inlet and the fluid outlet. Walls 46, 48 define in part the internal volume 45. The walls 46, 48 move away from each other when the device expands and towards each other when the device contracts. The walls 46, 48 are composed of a compliant material so that they may expand and contract depending on the flow requirements of the dialysis device. Suitable compliant materials include elastomers and plastics, such as natural rubber latex, PVC, polyurethane, or silicone.

The dialysis machine 30 may operate at a typical average flow rate of 500 ml/min, but the given instantaneous demand rate may be between 0 ml/min and 1000 ml/min. Thus, the lower fluid demand may be 0 ml/min, and the higher fluid demand may be 1000 ml/min. The fluid flow rate from the fluid source 10 is preferably generally equal to the average dialysis fluid demand of the dialysis machine 30. The flow regulation device 40 may provide a maximum internal volume between 25 ml and 200 ml, preferably between 50 mL and 100 mL. Thus, the flow regulation device 40 may provide for pulses of no flow and maximum flow of about 6-10 seconds. In one embodiment, the dialysis machine provides a flow cycle of between 5 and 60 seconds of fluid demand, and between 0.5 and 30 seconds of no fluid demand.

Figure 5:
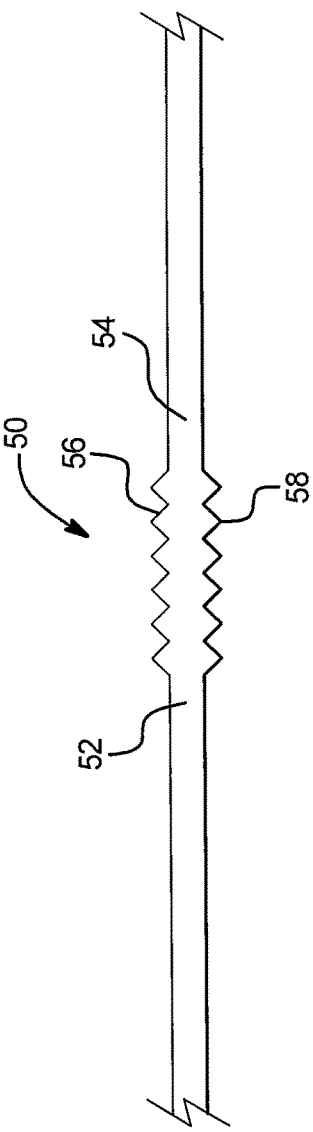
FIG. 5 illustrates another embodiment of a flow regulation device.

FIG. 5 illustrates another embodiment 50 of a flow regulation device. The flow regulation device 50 includes a fluid inlet 52 in fluid communication with the fluid source 10 and a fluid outlet 54 in fluid communication with the dialysis machine 30. The flow regulation device 50 includes at least one pleated wall 56 and optionally a second pleated wall 58. The pleats in the pleated walls 56, 58 allow the walls 56, 58 to expand outwardly and contract inwardly to provide a variable internal volume for the flow regulation device 50. The flow regulation device 50 may be made of any suitable material, including elastomers, plastics, and so forth.

The flow regulation devices 40, 50 may be easily sanitized between uses. Because the inner surfaces of the flow regulation devices 40, 50 are exposed to fluid (which may be a disinfecting solution), it is easy to ensure that the entire flow circuit has been disinfected.

Figure 6:
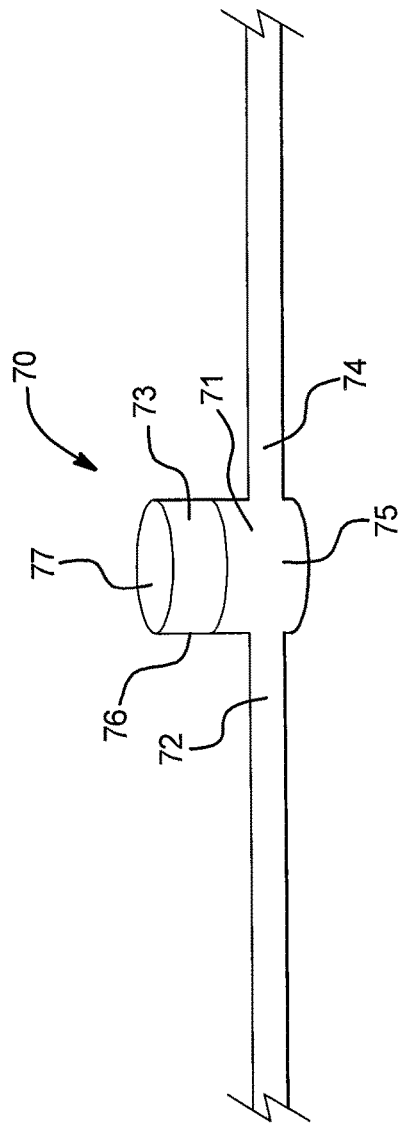
FIG. 6 illustrates another embodiment of a flow regulation device.

FIG. 6 illustrates another embodiment 70 of a flow regulation device. Flow regulation device 70 includes a rigid container 76 to regulate the required flow from the fluid source to the fluid demand of the dialysis machine. The container 76 includes dialysis fluid 71 in the bottom portion 75 and air or other gas 73 in the top portion 77. The level of the dialysis fluid 71 rises when the dialysis machine 30 has a lower demand and falls when the dialysis machine 30 has a higher demand and draws fluid from the container 76. To accommodate the change in the volume of the fluid 71, the air 73 also changes volume. To accommodate the change in air volume, the air 73 may be compressed or expanded as appropriate. Alternatively, air 73 may be discharged to the exterior of the flow regulation device 70 and taken into the device 70 to control the air volume. The intake of air is preferably through a suitably rated filter or other mechanism to maintain the sterility of the system.

The systems described herein provide significant advantages over current systems. By using a flow regulation device, changes in draw rate are smoothed so that the fluid supply 10 only needs to supply dialysis fluid at the average draw rate of the dialysis machine 30, not at the peak draw rate. The flow regulation devices 40, 50, 70 take up very little space and do not require the large tank volumes of conventional systems.

In another aspect, a dialysis system 10 uses a flow control method to accommodate the variations in fluid demand of the dialysis machine 30. The system includes a data connection between the dialysis machine 30 and the fluid source 10. The data connection provides a signal from the dialysis machine 30 to the fluid source 10 to adjust the flow setting of fluid from the fluid source 10. The flow setting may include a simple on/off control or a more precise flow control. The signal may be indicative of a current fluid demand of the dialysis machine 30, or the anticipated future demand. The dialysis machine 30 may include a control mechanism for its pumps. Based on the current and future flow need of the pumps, the dialysis machine 30 specifies the desired flow rate of the dialysis fluid. The output of the fluid source 10 is regulated to meet the real-time demand of the dialysis machine 30.

For example, the dialysis machine 30 sends a command signal to a valve or other flow setting to open the valve or provide a certain flow rate. Dialysis fluid (or purified water) from the fluid source 10 is then provided at the desired flow rate. The fluid source 10 would typically produce the fluid at the peak rate needed. When the fluid demand of the dialysis machine 30 is lowered, the dialysis machine 30 sends a command to slow or stop the production of dialysis fluid. The dialysis system may be programmed to anticipate the demand of the dialysis machine 30 so that there is no lag time between the dialysis fluid demand of the dialysis machine 30 and the desired flow rate of dialysis fluid from the fluid source 10. The connection between the dialysis machine 30 and the fluid source 10 may be provided by any type of data communication link, including wired, radio, infrared, Bluetooth, and the like.

In another embodiment, a system uses a fluid connection to convey information from the dialysis machine 30 to the fluid source 10. When the dialysis machine 30 draws fluid at the high rate, the fluid source 10 experiences a reduced pressure on an outlet line. A pressure transducer may be used to detect this pressure drop and increase the fluid generation rate accordingly. When the dialysis machine 30 reduces the draw rate, the pressure on the outlet line of the fluid source 10 will increase, which can be detected with the same pressure sensor, leading to a reduction in flow rate. This embodiment provides another means of conveying flow rate information.

The data connection allows the flow rate of the fluid from the fluid source 10 to be synchronized with the draw rate of the dialysis device 30. This prevents the fluid source (such as system 60) from having to consistently run at the peak draw rate of the dialysis machine 30. The life span of the components of the dialysis solution preparation system (such as pumps, filters, sensors, and so forth) can be extended by reducing their total use. Further, the fluid (whether dialysate or water) that is produced but not used for dialysis (and thus wasted) is limited, because it is not pumped when it is not needed.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A dialysis system comprising:
a dialysis machine with a variable fluid demand including at least a lower demand and a higher demand;
a purified water source in fluid communication with the dialysis machine and providing purified water to the dialysis machine at a fluid flow rate; and
a flow regulation device comprising a closed volume having a cross-sectional area larger than that of its purified water inlet and purified water outlet, the inlet in fluid communication with the purified water source, the outlet in fluid communication with the dialysis machine, the flow regulation device including a compliant material in sealed communication with the purified water inlet and the purified water outlet such that the purified water contacts the compliant material without passing through the compliant material, the compliant material operable to expand and contract to provide a variable internal volume, and wherein the compliant material of the flow regulation device expands when the dialysis machine has the lower demand and contracts when the dialysis machine has the higher demand.

2. The dialysis system of claim 1, wherein the dialysis machine produces dialysate from the purified water.

3. The dialysis system of claim 1 wherein the flow regulation device comprises a first wall and a second wall disposed opposite each other between the purified water inlet and the purified water outlet to define in part the internal volume, wherein the first wall and the second wall are composed of the compliant material.

4. The dialysis system of claim 3 wherein the first wall and the second wall move away from each other when the device expands and move towards each other when the device contracts.

5. The dialysis system of claim 1 wherein the flow regulation device comprises a pleated wall, the pleated wall expanding outwardly and contracting inwardly to provide the variable internal volume.

6. The dialysis system of claim 1 wherein the flow regulation device provides a maximum internal volume between 25 mL and 200 mL.

7. The dialysis system of claim 6 wherein the maximum internal volume of the flow regulation device is between 50 ml and 100 ml.

8. The dialysis system of claim 1 wherein the purified water source comprises a system for preparing the purified water from a water source.

9. The dialysis system of claim 1 wherein the fluid flow rate from the purified water source is generally constant.

10. The dialysis system of claim 9 wherein the fluid flow rate from the purified water source is generally equal to an average fluid demand of the dialysis machine.

11. The dialysis system of claim 1 wherein the dialysis machine is a hemodialysis machine.

12. A dialysis system comprising:
a dialysis machine with a variable fluid demand including at least a lower demand and a higher demand;
a fluid source in fluid communication with the dialysis machine and providing fluid to the dialysis machine at a fluid flow rate; and
a flow regulation device comprising a fluid inlet in fluid communication with the dialysis fluid source and a fluid outlet in fluid communication with the dialysis machine, wherein the flow regulation device contains a gas that contacts the fluid from the fluid source and provides a gas volume, and wherein the flow regulation device is configured to discharge gas from the flow regulation device and/or intake gas into the flow regulation device to regulate the gas volume to provide a variable fluid volume, the flow regulation device providing a maximum fluid volume between 25 mL and 200 mL, wherein the gas volume decreases when the dialysis machine has the lower demand and increases when the dialysis machine has the higher demand.

13. The dialysis system of claim 12 wherein the flow regulation device comprises a rigid canister.

14. The dialysis system of claim 12 wherein the gas volume is regulated by discharging gas from the flow regulation device and taking gas into the flow regulation device.

15. The dialysis system of claim 14 further comprising a filter for filtering gas entering the flow regulation device.

16. A dialysis system comprising:
a dialysis machine;
a dialysate production unit housed in the dialysis machine;
a purified water source in fluid communication with the dialysate production unit and providing fluid to the dialysis machine at a fluid flow rate;
a controller provided with the dialysis machine and configured to control a variable fluid demand of the dialysate production unit; and
a flow control mechanism including a closed volume having a cross-sectional diameter larger than its inlet and outlet diameters and including a compliant material, the flow control mechanism located between the purified water source and the dialysate production unit for storing purified water to help satisfy the variable fluid demand of the dialysate production unit.

17. The dialysis system of claim 16 wherein the flow control mechanism is actively controlled by the controller.

18. The dialysis system of claim 16 wherein the flow control mechanism includes a first wall and a second wall disposed opposite each other.

19. The dialysis system of claim 16, wherein the dialysate production unit includes at least one concentrate pump controlled by the controller, the concentrate pump affecting the variable demand of the dialysate production unit.

20. The dialysis system of claim 16, wherein the flow control mechanism includes a flexible portion that expands and contracts depending upon the fluid demand of the dialysate production unit, the flexible portion comprising the compliant material.

21. The dialysis system of claim 16, wherein the compliant material contacts purified water from the purified water source without passing through the compliant material.

22. A dialysis system comprising:
a dialysis machine with a variable fluid demand including at least a lower demand and a higher demand;

a purified water source in fluid communication with the dialysis machine and providing purified water to the dialysis machine at a fluid flow rate, the dialysis machine producing dialysate from the purified water; and a flow regulation device including a closed volume having a cross-sectional area larger than that of its purified water inlet and purified water outlet, the inlet in fluid communication with the purified water source, the flow regulation device including a compliant material in sealed communication with the purified water inlet and the purified water outlet such that the purified water contacts the compliant material, the contacting of the purified water performed without passing through the compliant material, the compliant material operable to expand and contract to provide a variable internal water volume, and wherein the variable internal water volume increases when the dialysis machine has the lower demand and the variable internal water volume decreases when the dialysis machine has the higher demand.

23. The dialysis system of claim 22, wherein the flow regulation device comprises a first wall and a second wall disposed opposite each other between the purified water inlet and the purified water outlet to define in part the internal water volume, wherein the first wall and the second wall are composed of the compliant material.

24. The dialysis system of claim 23, wherein the first wall and the second wall move away from each other when the device expands and move towards each other when the device contracts.

25. The dialysis system of claim 22, wherein the flow regulation device comprises a pleated wall, the pleated wall expanding outwardly and contracting inwardly to provide the variable internal water volume.

26. The dialysis system of claim 22, wherein the flow regulation device provides a maximum internal volume between 25 mL and 200 mL.

27. The dialysis system of claim 22, wherein the purified water source includes a system for preparing the purified water from a water source.

28. The dialysis system of claim 22, wherein the fluid flow rate from the purified water source is generally constant.

* * * * *